United States Patent [19]

Vermehren

[11] Patent Number: 5,550,237
[45] Date of Patent: Aug. 27, 1996

[54] PROCESS FOR THE PREPARATION OF CARBOXYARENESULFONIC ACIDS AND THEIR CARBOXYLIC ACID DERIVATIVES

[75] Inventor: Jan Vermehren, Idstein, Germany

[73] Assignee: Hoechst Schering AgrEvo GmbH, Berlin, Germany

[21] Appl. No.: 415,696

[22] Filed: Apr. 3, 1995

[30] Foreign Application Priority Data

Apr. 5, 1994 [DE] Germany .................. 44 11 682.9

[51] Int. Cl.$^6$ .................. C07C 309/58; C07D 295/192
[52] U.S. Cl. .................. 544/159; 558/250; 558/353; 560/14; 562/47; 562/56
[58] Field of Search .................. 562/56, 47

[56] References Cited

U.S. PATENT DOCUMENTS

| | | | |
|---|---|---|---|
| 4,145,349 | 3/1979 | Bebbington | 260/301 |
| 4,383,113 | 5/1983 | Levitt | 544/211 |

FOREIGN PATENT DOCUMENTS

| | | |
|---|---|---|
| 0007687 | 2/1980 | European Pat. Off. . |
| WO92/13845 | 8/1992 | WIPO . |

OTHER PUBLICATIONS

Nagira, K. et al., "Reaction of Diazonium Salts with Transition Metals. 4. Palladium(0)–Catalyzed Carboxylation of Arenediazonium Salts" J. Org. Chem. Jun. 1980, 45, 2365–2368.

Olah, G. et al., "Copper (II) Chloride Catalyzed Carboxydediazoniation of Arenediazonium Tetrafluoroborates With Carbon Monoxide in Aqueous Dioxane Solution to Arenecarboxylic Acids", Synlett Letters, (Received 4 Jul. 1990) p. 596.

Schoenberg, A. et al., "Palladium–Catalyzed Carboalkoxylation of Aryl, Benzyl, and Vinylic Halides" J. Org. Chem. vol. 39, No. 23, pp. 3318–3326; @1974.

*Primary Examiner*—Robert W. Ramsuer
*Assistant Examiner*—Laura L. Stockton
*Attorney, Agent, or Firm*—Curtis, Morris & Safford, P.C.

[57] ABSTRACT

Compounds (I) in which Ar is (substituted) arylene and Nuc is the radical of a nucleophile Nuc-H and which are valuable intermediates for pharmaceuticals, crop protection products and colorants $$HO_3S-Ar-CO-NUC \qquad (I)$$

can be prepared according to the invention by reacting an internal diazonium salt of the formula (II)

$$^\ominus O_3S-Ar-N_2^\oplus$$

with CO in the presence of a metal catalyst of group VIII of the Periodic System or Cu and Nuc-H or a salt thereof.

10 Claims, No Drawings

PROCESS FOR THE PREPARATION OF CARBOXYARENESULFONIC ACIDS AND THEIR CARBOXYLIC ACID DERIVATIVES

Compounds of the formula (A) or their salts

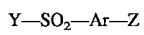    (A)

in which

Ar is an unsubstituted or substituted arylene radical,

Y is OH, amino, substituted or disubstituted amino or halogen and

Z is a carboxyl group or the functional group of a carboxylic acid derivative can be employed as intermediates in the preparation of medicaments, plant protection products and colorants (see, for example, EP-A-007687, (U.S. Pat. No. 4,383,113) WO 92/13845 and manuals on chemical synthesis).

To date, it has only been possible to prepare the compounds of the formula (A) using relatively complicated synthetic sequences, due to the number of reactive functional groups. In principle, processes for the preparation of compounds of the formula (A) differ with regard to sequence and method of introducing functional groups on the aromatic ring unit.

For example, WO 92/13845 discloses a preparation process for carbalkoxyiodobenzenesulfonyl chlorides, in which the $SO_2Cl$ group is introduced in the last synthesis step by reacting the diazonium salts of alkyl aminoiodobenzoates with $SO_2$ in the presence of copper chlorides. In the event that the amino group is in the ortho-position relative to the carbalkoxy group, a bisulfide is additionally formed as a by-product, and this must additionally be reacted with chlorine in order to convert it to the sulfonyl chloride. While even substantial amounts of the alkyl aminoiodobenzoates employed are accessible by standard processes, complicated synthetic routes are required if they are to be prepared from inexpensive compounds.

If the carboxyl function is to be introduced at the end of the synthesis chain, carbonylation methods may be regarded as suitable in principle. For example, metal-catalyzed, in particular palladium-catalyzed carbonylation reactions are known of aryl halides and of aryldiazonium tetrafluoroborates, during which processes esters of aromatic carboxylic acids or, after their hydrolysis, the free carboxylic acids are obtained (see, for example, J. Org. Chem. 39, 3318 (1974); J. Org. Chem. 45, 2365 (1980); JP-A-01-316364; G. A. Olah et al., Synlett 1990, 596). The known methods for the catalytic carbonylation have numerous disadvantages:

Carbonylation reactions of aryl halides are frequently unsuccessful, in particular in the case of compounds which have other functional groups such as, for example, iodine, since no sufficient selectivity can be achieved.

Owing to the $BF_4$ group, which is required, inter alia, for reasons of stability, the aryldiazonium tetrafluoroborates employed in the above alternatives for carbonylation methods are relatively expensive or not readily accessible, which limits their use on an industrial scale. Moreover, the applicability of the method is adversely affected by some functional groups in the molecule or the solvent; the presence of an alcohol, for example, results in unsatisfactory yields and by-products (J. Org. Chem. 45, 2365 (1980)).

It was therefore an object to provide a process for the preparation of compounds of the formula (I) which can be used on an industrial scale, whose starting materials are readily accessible and which avoids all or some of the abovementioned disadvantages.

Surprisingly, there has now been found an improved process of the type of catalytic carbonylation of diazonium salts of aromatic amino compounds, by which the abovementioned object is achieved.

The invention relates to a process for the preparation of compounds of the formula (I) or salts thereof,

    (I)

in which

Ar is an unsubstituted or substituted arylene radical, preferably an unsubstituted or substituted 1,2-, 1,3- or 1,4-phenylene radical, and Nuc is the radical of a nucleophile Nuc-H, which comprises reacting an internal diazonium salt of the formula (II)

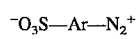    (II)

with carbon monoxide in the presence of a metal catalyst from the group composed of catalysts of metals of group VIII of the Periodic System and of copper, and with the nucleophile of the formula Nuc-H or a salt thereof.

In the above formulae (I) and (II) and hereinbelow, Ar is an optionally substituted arylene radical, the aromatic moiety being a carbocyclic aromatic, preferably 6-membered, ring, which is optionally benzo-fused. Examples of Ar are optionally substituted phenylene and naphthylene. Suitable substituents on the aromatic ring are one or more radicals which are generally possible on aromatic radicals and which are preferably known or customary. Examples of such substituents are alkyl, alkenyl, alkynyl, alkoxy, the last-mentioned four radicals being unsubstituted or substituted by one or more halogen atoms or one or more alkoxy radicals, and unsubstituted or substituted aryl, unsubstituted or substituted arylalkyl, halogen, nitro, cyano, sulfo, acyl, alkylsulfonyl, haloalkylsulfonyl, alkylthio, unsubstituted or substituted aryloxy, hydroxyl, monoalkylamino, dialkylamino and acylamino. Preferred amongst the carbon-containing substituents are those with 1 to 6 carbon atoms, preferably 1 to 4 carbon atoms. Excepted are, naturally, amassments or combinations of substituents which are incompatible with the stability of the compounds (I) and (II).

Aryl, also in composite meanings such as arylalkyl or aryloxy, is an aromatic radical, for example phenyl or naphthyl. The abovementioned substituents on the aromatic ring of Ar are, in principle, also suitable as substituents for aryl or on the aryl moiety in arylalkyl or aryloxy, but unduly large molecules for (I) and (II) should be avoided, i.e. arylalkyl which is substituted by arylalkyl, or phenoxy which is substituted by phenoxy, will only be useful in individual cases.

Acyl is, for example, formyl, alkylcarbonyl, alkoxycarbonyl, unsubstituted or substituted carboxamide, such as N-monoalkylcarboxamide and N,N-dialkylcarboxamide, alkyl having 1 to 6 carbon atoms, in particular 1 to 4 carbon atoms, being preferred in the composite meanings; acyl is, furthermore, arylcarbonyl such as, for example, unsubstituted or substituted benzoyl. Acyl is particularly ($C_1$–$C_4$-alkyl)carbonyl.

The term "internal diazonium salt" of the formula (II) embraces, in addition to the compounds without foreign cations and foreign anions, also those in which the sulfonate group is coordinated with foreign cations such as, for example, $Na^+$ and $K^+$, and the diazonium group is coordinated with foreign anions, such as, for example, $Cl^-$ and one $SO_4^-$ equivalent.

Ar is preferably a 1,2-, 1,3- or 1,4-phenylene radical which is unsubstituted or substituted by one or two radicals selected from the group composed of $C_1$–$C_4$-alkyl, $C_1$–$C_4$- haloalkyl, $C_2$–$C_4$-alkenyl, $C_2$–$C_4$-alkynyl, $C_1$–$C_4$-alkoxy, benzyl, halogen, nitro, cyano, ($C_1$–$C_4$-alkyl)carbonyl, $C_1$–$C_4$-alkylsulfonyl, $C_1$–$C_4$-alkylthio, phenoxy, hydroxyl, mono($C_1$–$C_4$-alkyl)amino and di($C_1$–$C_4$-alkyl)amino. 1,2-, 1,3- or 1,4-phenylene which is unsubstituted or substituted by one or two radicals selected from the group composed of methyl, ethyl, methoxy, ethoxy, halogen, such as fluorine, chlorine, bromine and iodine, and nitro, cyano, ($C_1$–$C_3$-alkyl)carbonyl, such as acetyl, and $C_1$–$C_4$-alkylsulfonyl, such as methyl- or ethylsulfonyl, and hydroxyl as well as di($C_1$–$C_4$-alkyl)amino, such as dimethylamino, is of particular interest; halogen is particularly preferred in this context.

Nuc is the radical of the nucleophile Nuc-H or of a salt thereof, which is reacted according to the invention with the internal diazonium salt (II). Suitable as a nucleophile is a broad range of compounds which have a great variety of structures but must have an exchangeable hydrogen atom ("acidic H") or, in the case of the salt, an exchangeable cation. Known as customary nucleophiles are, for example, compounds having reactive functional OH, NH or SH groups or their salts, and, as a rule, these can be employed according to the invention.

Thus, the nucleophiles Nuc-H or the salts thereof are, for example, compounds from the group composed of alcohols and their salts, primary and secondary amines, mercaptans, carboxylic acids and their salts; but ammonia is also suitable as a nucleophile. Water is less suitable in most cases as nucleophile Nuc-H, since, as a rule, water results in secondary reactions with the diazonium salt (II). In individual cases, when suitable solvent combinations are used, water is also suitable as the nucleophile Nuc-H. Examples of reactive compounds Nuc-H are aliphatic alcohols, such as the alkanols methanol, ethanol, n- and i-propanol, n-, i-, t- and 2-butanol, and aromatic alcohols, such as unsubstituted and substituted phenol or naphthol, and their salts, aliphatic amines, such as methylamine, dimethylamine, morpholine and aromatic amines, such as unsubstituted and substituted aniline, alkylthio compounds, such as methylmercaptan, and aliphatic and aromatic carboxylic acids and, preferably, their salts, such as formic acid and formates, acetic acid and acetates, propionic acid and propionates, benzoic acid and benzoates.

Accordingly, for example,

Nuc is a radical of the formula OH, $OR^1$, O—CO—$R^2$, $SR^3$ or $NR^4R^5$, in which $R^1$ is alkyl, alkenyl or alkynyl, the last-mentioned three radicals being unsubstituted or substituted by one or more radicals selected from the group composed of halogen, hydroxyl, alkoxy, alkylthio, cyano, nitro, carboxyl, carbalkoxy, amino, monoalkylamino and dialkylamino, or is unsubstituted or substituted aryl, or unsubstituted or substituted arylalkyl, preferably alkyl which is unsubstituted or substituted by one or more halogen atoms or by one or more alkoxy radicals, or unsubstituted or substituted aryl, or unsubstituted or substituted arylalkyl, $R^2$ is hydrogen or a radical analogous to $R^1$, preferably alkyl which is unsubstituted or substituted by one or more radicals selected from the group composed of halogen, alkoxy, alkylthio, cyano, nitro, carbalkoxy and dialkylamino, or unsubstituted or substituted aryl, or unsubstituted or substituted arylalkyl, $R^3$ is a radical analogous to $R^1$, preferably alkyl which unsubstituted or substituted by one or more radicals selected from the group composed of halogen, alkoxy and alkylthio, $R^4$ is hydrogen, acyl or a radical analogous to $R^1$, preferably hydrogen, alkyl, acyl or unsubstituted or substituted aryl, and $R^5$ is hydrogen, acyl or a radical analogous to $R^1$, preferably hydrogen, alkyl, acyl or unsubstituted or substituted aryl;

the symbols aryl and acyl have the meanings already explained further above; preferred amongst the carbon-containing substituents are those having 1 to 6 carbon atoms, preferably 1 to 4 carbon atoms.

The compounds of the formula (I) are obtained in the form of the free sulfonic acids or in the form of their salts, depending on the pH at which the compounds (I) are isolated. For economic reasons, especially suitable salts are alkali salts and alkaline earth metal salts, in particular the alkali metal salts, such as sodium and potassium salts.

In most cases, it is expedient to carry out the reaction according to the invention of the internal diazonium salts (II) in the presence of an organic solvent, which may also be a mixture of a plurality of organic solvents. Examples of suitable solvents are nonpolar solvents and, preferably, polar protic or aprotic dipolar solvents and their mixtures. In individual cases, aqueous-organic solvents may also be employed according to the invention, but substantially anhydrous solvents are preferably used in order to avoid secondary reactions.

Examples of suitable solvents are ethers, such as diethyl ether, tetrahydrofuran (THF), dioxane, diglyme and tetraglyme, amides, such as dimethylformamide (DMF), dimethylacetamide and N-methylpyrrolidone, ketones, such as acetone, nitriles, such as acetonitrile, propionitrile, butyronitrile and benzonitrile, sulfoxides and sulfones, such as dimethyl sulfoxide (DMSO) and sulfolane, halogenated aliphatic and aromatic hydrocarbons, such as methylene chloride and chlorobenzene.

Alcohols, such as the alkanols methanol, ethanol, n- and i-propanol and n-, i-, t- and 2-butanol, may frequently also be employed, especially in combinations of solvents.

Suitable metal catalysts of group VIII of the Periodic System are, for example, the metals having the chemical symbols Co, Ni, Pd, Pt, Rh, Ir and Os, all of which can be employed in the form of the free metals, on a support (for example silica gel or charcoal), as a metal salt (for example $CoCl_2$) or as a metal complex. Most of these catalysts are already known as catalysts for carbonylation reactions (see the abovementioned references).

Examples of suitable catalysts are palladium diacetate [Pd(OAc)$_2$], bis(dibenzylideneacetone)palladium [Pd(dba)$_2$], tetrakis(triphenylphosphane)palladium [Pd(P(C$_6$H$_5$)$_3$)$_4$], tetrakis(tritolylphosphane)palladium [Pd(P(C$_7$H$_7$)$_3$)$_4$], Pd/charcoal, bis(triphenylphosphane)palladium dichloride [Pd (P(C$_6$H$_5$)$_3$)$_2$Cl$_2$] and complexes of the type nickel-his (diphenylphosphinealkylene) dichloride, "alkylene" being, for example, $C_2$–$C_4$-alkylene.

A catalyst which can also be employed is copper, for example in the form of the Cu(I) or Cu(II) salts, such as $CuCl_2$.

The catalyst which is preferably employed according to the invention is palladium in the abovementioned use forms, in particular palladium diacetate or palladium/charcoal.

As a rule, the process according to the invention is carried out in such a way that a solution or suspension of the internal diazonium salt (II) is first prepared, for example by dissolving or suspending the separately prepared salt, or by directly using the reaction mixture after diazotization of the appropriate aminoarenesulfonic acid.

For the carbonylation, the necessary catalyst is added, if appropriate after addition of organic solvent and, if hitherto not present, the nucleophile Nuc-H or a salt thereof, and carbon monoxide is fed in. CO can be fed in for example by passing in or injecting under pressure, the conversion rate depending on the pressure prevailing in each case.

The optimum pressure for a technical-scale process can be readily determined by preliminary experiments and is, as a rule, between 1 and 120 bar ($10^5$ to $120 \cdot 10^5$ Pascal), preferably between 1 and 50 bar, in particular between 3 and 15 bar. The pressure data preferably refer to the partial pressure of CO. The carbon monoxide can be fed in for example as a pure gas; however, gas mixtures containing CO, for example synthesis gas (CO+$H_2$) or gas mixtures of CO with nitrogen or other gases which are inert under the reaction conditions, can also be employed. When carrying out the reaction under superatmospheric pressure, it is expedient to use customary apparatus such as pressurized vessels, autoclaves, bomb tubes and the like.

The reaction temperature for the carbonylation should be selected sufficiently low to avoid endangering the stability of the diazonium salt. As a rule, the carbonylation reaction is carried out in a range from $-78°$ C. up to the decomposition temperature of the diazonium salt, preferably from $-50°$ to $+100°$ C., in particular $-20°$ to $+50°$ C.

Moreover, the conversion rate can depend on the ratio of the compound (II) to the amount of catalyst and on the concentration of the catalyst; however, in most cases, the ratio can be varied within a substantial range. Based on weight, the ratio of (II): catalyst is preferably in the range of 10,000:1 to 1:1, in particular 1000:1 to 10:1.

The carbonylation process can be carried out relatively easily from the technological point of view, either batchwise or continuously, and affords good yields. This advantageous result could not have been expected. Surprisingly, the internal diazonium salts (II) can be employed according to the invention without it being necessary to convert them into tetrafluoroborates. Moreover, it could not have been expected that the aromatic sulfonyl groups, which are known for having a powerful effect on the electronic conditions of the aromatic ring, would have virtually no adverse effect on the carbonylation reaction as such as well as on the selectivity of the carbonylation in the presence of other groups which are reactive in principle, such as halogen atoms.

Some of the internal diazonium salts (II) to be employed according to the invention in the carbonylation stage are novel; for example, compounds of the formula (II) in which Ar is phenylene which is substituted by one or two iodine atoms are novel and also a subject of the invention. The known and the novel compounds of the formula (II) can be prepared from the appropriate aminoarenesulfonic acids analogously to known methods (see, for example, Houben-Weyl, Meth. d. Org. Chem. [Methods in Organic Chemistry], Vol. X/3, page 16 et seq. and Vol. E16/2). In this context, it is possible, for example, to prepare the diazonium arenesulfonate (II) either in an aqueous medium using a diazotization reagent, such as nitrous acid or nitrosylsulfuric acid, subsequently isolate the product and transfer it into an organic medium, or else the diazonium arenesulfonate (II) can be prepared directly in the solvent to be used in the subsequent carbonylation reaction, using a diazotization reagent such as alkyl nitrite or nitrosylsulfuric acid.

It is known that isolated aryldiazonium sulfonates can decompose in an explosive fashion (Houben-Weyl, Methoden d. org. Chemie [Methods in Organic Chemistry], Vol. X, 3, p. 32 et seq.; H. Wichelhaus, Chem. Ber. 1901, 34, 11).

To improve the stability of the internal diazonium salt to spontaneous or explosive decomposition, a variety of inert substances can be added, preferably before the internal diazonium salt is isolated or before directly processing the reaction mixture.

Suitable stabilizing inert substances are, for example, organic solvents as they have already been mentioned as solvents for the carbonylation to give the compound (I), preferably aromatic hydrocarbons such as xylene, or nitriles such as acetonitrile, or alcohols such as t-butanol. Other suitable inorganic inert substances are, for example, mineral salts or kieselguhr, or organic inert substances, for example active charcoal, polyoxymethylene, polypropylene or polyethylene. The stabilizing inert substances are preferably added to the aqueous reaction mixture before the internal diazonium salts are isolated or before the reaction mixture is directly used for the carbonylation.

The general reaction sequence for the combined process variant, which includes the preparation of the diazonium arenesulfonate (II), is shown in Diagram 1 with aminobenzenesulfonic acids (III) as an example:

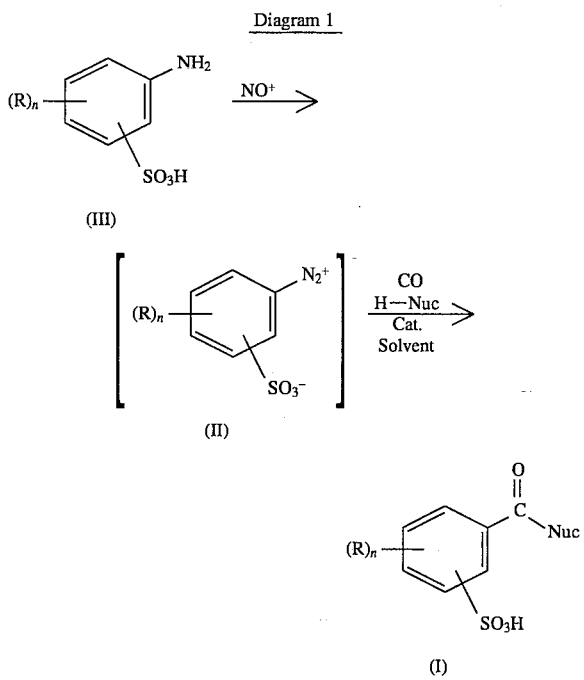

The basic aminoarenesulfonic acids, preferably anilinesulfonic acids (III), are inexpensive compounds which can be prepared on an industrial scale (see, for example, sulfonation of optionally substituted anilines in Houben-Weyl, Meth. d. Org. Chem. [Methods in Organic Chemistry], Vol. IX, 465 et seq., 512 et seq.) or can be converted into the desired compounds (III) starting from inexpensive simple substituted aminoarenesulfonic acids or anilinesulfonic acids by a large number of suitable derivatization reactions; see, for example, the iodination of anilinesulfonic acids in J. Chem. Soc. 1909, 1683).

The crude products obtained after the carbonylation are compounds of the formula (I) or salts thereof, depending on the pH at which the product is isolated. To work up the reaction batch, the isolation and purification methods customary in laboratory and process technology, such as, for example, crystallization, extraction, distillation and chromatography, can be used if desired. Especially in the case of larger batches, it is expedient to recover the catalyst and to use it for the next batch.

In some cases, the products of the formula (I) themselves are highly reactive intermediates such as, for example, anhydrides or activated esters; they can be processed advantageously in a subsequent step, either directly or after brief intermediate isolation, to give more stable products of the formula (I) or different products; frequently, alkaline hydrolysis is useful first in the case of anhydrides as the primary main product, to give the free carboxylic acid (II) where Nuc=OH.

In general, the compounds of the formula (I) or their salts are suitable intermediates for the preparation of important use products, such as pharmaceuticals, crop protection products and colorants, or they can be converted into the desired intermediates of the abovementioned formula (A) with the aid of a large number of standard methods. Particularly interesting is processing to obtain sulfonyl chlorides and sulfonamides; see, for example, sulfonyl chlorides by the method given in Houben-Weyl, Meth. d. Org. Chem. [Methods in Organic Chemistry], Vol. IX, 564 et seq., and sulfonamides by the method given in Houben-Weyl, Meth. d. Org. Chem. [Methods in Organic Chemistry], Vol. IX, 605 et seq.

EXAMPLES

1) Monosodium 5-iodocarboxybenzenesulfonate

1a) Preparation of the diazonium salt 7.5 g (25.1 mmol) of 2-amino-5-iodobenzenesulfonic acid are suspended in 20 ml of water and diazotized at 0° C. by adding 1.64 ml of concentrated sulfuric acid and 1.82 g of sodium nitrite in 5 ml of water. The mixture is subsequently stirred for 1 hour and filtered off with suction, and the solids are washed in each case twice using methanol and diethyl ether. This gives 2-diazonium- 5-iodobenzenesulfonate as a pale yellow powder with a point of decomposition of 143° C. and the following NMR data:

$^1$H-NMR (D$_2$O): δ[ppm]=8.95 (d, 1H); 8.35 (dd, 1H); 8.21 (d, 1H)

1b) Carbonylation

The diazonium salt obtained in 1a) is suspended in 75 ml of acetonitrile. After 4.92 g of sodium acetate and 0.22 g of palladium diacetate have been added, the mixture is introduced into an autoclave at 0° C. and, after 10 bar of carbon monoxide have been injected, shaken vigorously for 2 hours. After releasing the pressure in the autoclave, the reaction mixture is filtered, the residue is stirred for 1 hour with 50 ml of 20% sodium hydroxide solution, and the pH is brought to 1 using concentrated hydrochloric acid, whereupon the product precipitates. After drying of the product, 5.5 g (63% of theory) of monosodium 5-iodocarboxybenzenesulfonate are obtained as a white powder. The mother liquor still contains substantial amounts of product and can be recirculated to the hydrolysis step of the next batch. Physical data of the product obtained:

Melting point (m.p.) above 280° C. $^1$H-NMR (D$_2$O): δ[ppm]=8.15 (d, 1H); 7.84 (dd, 1H); 7.19 (d, 1H)

2) 5-Iodo-2-methoxycarbonylbenzenesulfonic acid

Variant 2a)

22.5 g of 2-amino-5-iodobenzenesulfonic acid are finely suspended in 150 ml of acetonitrile, and 4.18 ml of concentrated sulfuric acid are added. The mixture is diazotized using 7.73 g of n-butyl nitrite at 25° C., and the excess of butyl nitrite is subsequently destroyed using amidosulfonic acid. The suspension obtained is treated with 9.13 ml of methanol and 1.0 g of palladium/charcoal (10%, water content 50%) and transferred to a 1-liter autoclave. After the autoclave has been flushed with protective gas, carbon monoxide is injected with a pressure of 10 bar. After a reaction time of 2 hours with vigorous shaking at room temperature, the pressure is released, the autoclave is flushed with protective gas and the reaction solution is filtered. The filtrate is evaporated under reduced pressure, and 24.6 g (95% of theory) of 5-iodo-2-methoxycarbonylbenzenesulfonic acid are obtained in the form of a dark oil which crystallizes slowly upon standing. NMR data of the product:

$^1$H-NMR (DMSO-d$_6$): δ[ppm]=8.03 [(d); 1H]; 7.76 [(dd); 1H]; 7.10 [(d); 1H]; 3.72 [(s); 3H; 9.3 [(s), broad]

Variant 2b)

16 g of a diazonium salt obtained as described in Example 1a) are treated with 1.0 g of palladium/charcoal (10%, water content 504) and 6.28 ml of methanol and transferred to a 1-liter autoclave. After flushing with protective gas, synthesis gas (50% by volume of CO and 50% by volume of H$_2$) is injected with a pressure of 20 bar. After a reaction time of 4 hours with vigorous shaking at room temperature, the pressure is released, the autoclave is flushed with protective gas and the reaction solution is filtered. The filtrate is evaporated under reduced pressure, and 14.2 g (84% of theory) of 5-iodo-2-methoxycarbonylbenzenesulfonic acid are obtained in the form of a dark oil which slowly crystallizes on standing. NMR data of the product as in Variant 2a).

Variant 2c)

25 g (81 mmol) of 2-amino-5-iodobenzenesulfonic acid are suspended in 100 ml of water and diazotized using 27.8 g (87.6 mmol) of nitrosylsulfuric acid (40%). When the diazotization is complete, the excess nitrosyl is destroyed by a small amount of amidosulfonic acid. 75 g of kieselguhr are added to the suspension obtained, and, after 50 ml of water have been added, mixed in vigorously. The mixture is subjected to filtration with suction, and the residue is washed in each case twice with water and methanol and once with acetonitrile. The mixture is dried by allowing it to stand in the air. This gives 97.3 g of the internal diazonium salt on kieselguhr, which is suspended in 200 ml of acetonitrile. At 25° C., 2 g of palladium/charcoal (type Degussa E10 N/W) and 8.85 ml (0.21 mol) of methanol are added. The mixture is transferred to a 1-1 autoclave which is flushed twice with carbon monoxide. The autoclave is sealed, and 10 bar of CO are injected. The mixture is allowed to react for 4 hours at 25° C. with vigorous stirring. The pressure is released, the autoclave is flushed twice with nitrogen, and the content is subjected to filtration. The residue is washed with acetonitrile, and the purified filtrate is freed from the solvent in vacuo. This gives 25.5 g of a dark oil. It contains 80.1% of pure 5-iodo-2-methoxycarboaylbenzenesulfonic acid.

EXAMPLES 3–31

The compounds of the formula (Ia) listed in Table I below are obtained from appropriately substituted aminobenzenesulfonic acids (III) analogously to Examples 1 and 2:

TABLE 1

Compounds of the formula (Ia)

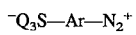

$$n = 0\text{--}2$$

| Ex. No. | $(R)_n$ | n | Nuc | Position of $SO_3M$ | M |
|---|---|---|---|---|---|
| 3 | — | 0 | $OCH_3$ | 2 | H |
| 4 | — | 0 | $OCH_3$ | 3 | H |
| 5 | — | 0 | $OCH_3$ | 4 | H |
| 6 | 2-Cl | 1 | $OCH_3$ | 4 | H |
| 7 | 4-Cl | 1 | $OCH_3$ | 2 | H |
| 8 | 2-F | 1 | $OCH_3$ | 4 | H |
| 9 | 4-Br | 1 | $OCH_3$ | 2 | H |
| 10 | 4,6-$I_2$ | 2 | $OCH_3$ | 2 | H |
| 11 | 4-$NO_2$ | 1 | $OCH_3$ | 2 | H |
| 12 | 4-CN | 1 | $OCH_3$ | 2 | H |
| 13 | 4-I | 1 | $O-CO-CH_3$ | 2 | Na |
| 14 | 4-I | 1 | $N(C_2H_5)_2$ | 2 | H |
| 15 | 4-I | 1 | $NH-C_6H_5$ | 2 | H |
| 16 | 4-I | 1 | N-morpholinyl | 2 | H |
| 17 | — | 0 | OH | 2 | Na |
| 18 | — | 0 | OH | 3 | Na |
| 19 | — | 0 | OH | 4 | Na |
| 20 | 4-Cl | 1 | OH | 2 | Na |
| 21 | 2-Cl | 1 | OH | 4 | Na |
| 22 | 4-Br | 1 | OH | 2 | Na |
| 23 | 4,6-$I_2$ | 2 | OH | 2 | Na |
| 24 | 4-$CH_3$ | 1 | OH | 2 | Na |
| 25 | 2-$CH_3$ | 1 | OH | 2 | Na |
| 26 | 4-OH | 1 | OH | 2 | Na |
| 27 | 4-$COCH_3$ | 1 | OH | 2 | Na |
| 28 | 4-CN | 1 | OH | 2 | Na |
| 29 | 4-$SO_2CH_3$ | 1 | OH | 2 | Na |
| 30 | 4-$NO_2$ | 1 | OH | 2 | Na |
| 31 | — | 0 | $S-CH_2-C_6H_5$ | 2 | H |
| 32 | 4-$CH_3$ | 1 | $OCH_3$ | 2 | H |

Characteristic data of compounds of Table 1:

The compound of Example No. 3 is an oil with the following chemical shifts in the $^1$H-NMR spectrum in DMSO-$d^6$:

δ[ppm]=7.74 [dd; 1H]; 7.45 [td; 1H], 7.38 [td; 1H]; 7.28 [dd, 1H]; 3.72 [s; 3H]

The compound of Example No. 7 is an oil with the following chemical shifts in the 1H-NMR spectrum in DMSO-$d^6$:

δ[ppm]=8.73 [broad; $SO_3H$]; 7.71 [d; 1H]; 7.49 [dd; 1H]; 7.36 [d; 1H]; 3.73 [s, 3H]

The compound of Example No. 32 forms greasy crystals with the following $^1$H-NMR resonances in DMSO-$d^6$:

δ[ppm]=7.54 [d; 1H]; 7.51 [broad; $SO_3H$]; 7.18 [d; 1H]; 7.16 [s; 1H]; 3.69 [s, 3H]; 2.33 [s; 3H]

I claim:

1. A process for the preparation of compounds of the formula (I) or salts thereof $$HO_3S-Ar-CO-Nuc \qquad (I)$$

in which

Ar is an unsubstituted or substituted arylene radical, and

Nuc is the radical of a nucleophile Nuc-H, which comprises reacting an internal diazonium salt of the formula (II)

$$^-O_3S-Ar-N_2^+ \qquad (II)$$

with carbon monoxide in the presence of a metal catalyst from the group composed of catalysts of metals of group VIII of the Periodic System and of copper, and with the nucleophile of the formula Nuc-H or a salt thereof.

2. The process as claimed in claim 1, wherein the metal catalysts employed are selected from the group composed of Co, Ni, Pd, Pt, Rh, Ir, Os and Cu.

3. The process as claimed in claim 1, wherein palladium catalysts are employed.

4. The process as claimed in claim 1, wherein the reaction is carried out at a pressure of 1 to 120 bar and a temperature of −78° C. up to the decomposition temperature of the diazonium salt (II).

5. The process as claimed in claim 4, wherein the pressure is 1 to 50 bar and the temperature is −50° to +100° C.

6. The process as claimed in claim 1, wherein the reaction is carried out in the presence of an organic solvent, which may also be a mixture of a plurality of organic solvents.

7. The process as claimed in claim 6, wherein the organic solvent is a polar protic or aprotic dipolar solvent from the group composed of ethers, amides, ketones, nitriles, sulfoxides, sulfones, alcohols, halogenated aliphatic hydrocarbons and halogenated aromatic hydrocarbons, or mixtures of these.

8. The process as claimed in claim 1, wherein Nuc-H or the salt thereof employed is selected from the group composed of alcohols and their salts, primary and secondary amines, mercaptans, carboxylic acids and their salts, ammonia and water.

9. The process as claimed in claim 8, wherein

Nuc is OH, $OR^1$, $O-CO-R^2$, $SR^3$ or $NR^4R^5$, $R^1$ is alkyl, alkenyl or alkynyl, the last-mentioned three radicals being unsubstituted or substituted by one or more radicals selected from the group composed of halogen, hydroxyl, alkoxy, alkylthio, cyano, nitro, carboxyl and carbalkoxy, amino, monoalkylamino and dialkylamino, or is unsubstituted or substituted aryl, or unsubstituted or substituted arylalkyl, $R^2$ is hydrogen or a radical selected from the group consisting of the radicals of $R^1$, $R^3$ is a radical selected from the group consisting of the radicals of $R^1$, $R^4$ is hydrogen, acyl or a radical selected from the group consisting of the radicals of $R^1$, and $R^5$ is hydrogen, acyl or a radical selected from the group consisting of the radicals of $R^1$.

10. The process as claimed in claim 1, wherein Ar is a 1,2-, 1,3- or 1,4-phenylene radical which is unsubstituted or substituted by one or two radicals selected from the group composed of $C_1$–$C_4$-alkyl, $C_1$–$C_4$-haloalkyl, $C_2$–$C_4$-alkenyl, $C_2$–$C_4$-alkynyl, $C_1$–$C_4$-alkoxy, benzyl, halogen, nitro, cyano, ($C_1$–$C_4$-alkyl) carbonyl, $C_1$–$C_4$-alkylsulfonyl, $C_1$–$C_4$-alkylthio, phenoxy, hydroxyl, mono($C_1$–$C_4$-alkyl) amino and di($C_1C_4$ -alkyl)amino.

* * * * *